(12) United States Patent
Scott

(10) Patent No.: US 10,406,035 B1
(45) Date of Patent: Sep. 10, 2019

(54) SLEEP MASK

(71) Applicant: Susan A. Scott, Virginia Beach, VA (US)

(72) Inventor: Susan A. Scott, Virginia Beach, VA (US)

( * ) Notice: Subject to any disclaimer, the term of this patent is extended or adjusted under 35 U.S.C. 154(b) by 58 days.

(21) Appl. No.: 15/832,367

(22) Filed: Dec. 5, 2017

(51) Int. Cl.
*A61F 9/04* (2006.01)
*A61K 9/00* (2006.01)
*A45D 44/00* (2006.01)

(52) U.S. Cl.
CPC .............. *A61F 9/04* (2013.01); *A45D 44/002* (2013.01); *A61K 9/007* (2013.01)

(58) Field of Classification Search
CPC .................................. A41D 13/11; A61F 9/04
USPC ........................................... 2/9, 15, 206, 174
See application file for complete search history.

(56) References Cited

U.S. PATENT DOCUMENTS

| | | | | |
|---|---|---|---|---|
| 1,743,801 A * | 1/1930 | Reynolds | ................... | A61F 9/04 2/15 |
| 1,926,926 A * | 9/1933 | Whitman | ............... | A45D 44/22 2/15 |
| 2,874,385 A * | 2/1959 | Wade | ........................ | A61F 9/04 2/15 |
| 2,891,252 A * | 6/1959 | Lazo | ....................... | A61H 39/04 2/15 |
| D302,167 S | 7/1989 | Sherman | | |
| 5,343,561 A | 9/1994 | Adam | | |
| D388,812 S | 1/1998 | Miehe et al. | | |
| 6,578,578 B2 | 6/2003 | Luquire | | |
| 7,603,723 B2 | 10/2009 | Ulm | | |
| 8,239,987 B2 | 8/2012 | Sharp | | |
| 8,852,073 B2 | 10/2014 | Genereux et al. | | |
| D717,362 S | 11/2014 | Kaufer | | |
| 8,932,199 B2 | 1/2015 | Berka et al. | | |
| D722,727 S | 2/2015 | Maruyama et al. | | |
| 9,138,086 B1 | 9/2015 | Bamberg | | |
| 2005/0229281 A1 * | 10/2005 | Glasser | ..................... | A61F 9/04 2/15 |
| 2012/0144556 A1 * | 6/2012 | Fiebel | .................... | A41D 13/11 2/206 |
| 2013/0131613 A1 * | 5/2013 | Elkins | ................... | A61M 35/00 604/303 |
| 2016/0000607 A1 | 1/2016 | Bamberg | | |

FOREIGN PATENT DOCUMENTS

CN 202456518 10/2012

* cited by examiner

*Primary Examiner* — Gloria M Hale
(74) *Attorney, Agent, or Firm* — Shaddock Law Group, PC

(57) ABSTRACT

A sleep mask having a mask body with a central portion formed between two extension portions; an ear loop extending from each of the extension portions, wherein each ear loop is attached or coupled to the extension portion proximate terminal ends of the ear loop; and a scent diffusing area formed within each of the extension portions, wherein each of the scent diffusing areas is capable of being at least partially infused with an aroma compound.

20 Claims, 4 Drawing Sheets

SLEEP MASK

CROSS-REFERENCE TO RELATED APPLICATIONS

Not Applicable.

STATEMENT REGARDING FEDERALLY SPONSORED RESEARCH OR DEVELOPMENT

Not Applicable.

REFERENCE TO SEQUENCE LISTING, A TABLE, OR A COMPUTER PROGRAM LISTING COMPACT DISC APPENDIX

Not Applicable.

NOTICE OF COPYRIGHTED MATERIAL

The disclosure of this patent document contains material that is subject to copyright protection. The copyright owner has no objection to the reproduction by anyone of the patent document or the patent disclosure, as it appears in the Patent and Trademark Office patent file or records, but otherwise reserves all copyright rights whatsoever. Unless otherwise noted, all trademarks and service marks identified herein are owned by the applicant.

BACKGROUND OF THE PRESENT DISCLOSURE

1. Field of the Present Disclosure

The present disclosure relates generally to the field of sleep masks. More specifically, the present disclosure relates to a disposable or therapeutic sleep mask.

2. Description of Related Art

It is generally known to have sleep masks that cover a wearer's eyes to provide a dark environment for the wearer to rest. The typical sleep mask attaches to the user's head by an elastic strap that extends from opposing ends of the mask and is placed around the wearer's head.

Additionally, sleep masks are typically formed of a material that renders the mask relatively expensive.

Any discussion of documents, acts, materials, devices, articles, or the like, which has been included in the present specification is not to be taken as an admission that any or all of these matters form part of the prior art base or were common general knowledge in the field relevant to the present disclosure as it existed before the priority date of each claim of this application.

BRIEF SUMMARY OF THE PRESENT DISCLOSURE

However, the typical sleep mask arrangement and construction materials have various shortcomings.

To overcome various shortcomings of the presently known sleep masks, the sleep mask of the present disclosure is generally formed of a material that allows the sleep mask to be inexpensively mass-produced, such that the sleep mask of the present disclosure can be disposable. This provides a way for a wearer to have a fresh, sanitary sleep mask at each use.

Additionally, the sleep mask of the present disclosure includes ear loops extending from opposing end portions of the sleep mask. By utilizing ear loops, the mask can be worn by placing each of the ear loops around a wearer's ear. In this manner, an attachment strap does not extend completely around the user's head. When an attachment strap extends around a wearer's head, it can interfere with the wearer's hair or result in a visible indention, similar to the visible line or indention created by "hat head", being left in the wearer's hair.

Furthermore, the sleep mask of the present disclosure provides scent diffusing areas that are formed in extension portions of the sleep mask, which are capable of being at least partially infused with an aroma compound. When the sleep mask of the present disclosure is worn, the extension portions of the sleep mask cover the temple areas of the wearer's head, so that an aroma compound can be diffused from the scent diffusing areas to an area proximate the wearer's temples.

In various exemplary, non-limiting embodiments, the sleep mask of the present disclosure comprises a mask body having a central portion formed between two extension portions; an ear loop extending from each of the extension portions, wherein each ear loop is attached or coupled to the extension portion proximate terminal ends of the ear loop; and a scent diffusing area formed within each of the extension portions, wherein each of the scent diffusing areas is capable of being at least partially infused with an aroma compound.

In various exemplary embodiments, the mask body is a continuous mask body that may optionally be formed of a Polyspunbond, a Spunbond Polypropylene, a Spunbond Polyester, a single layer nonwoven material, or a multilayer nonwoven material.

In various exemplary embodiments, the mask body comprises a single layer of material. Alternatively, the mask body may optionally comprise two or more layers of material that are at least partially attached or coupled together.

In various exemplary embodiments, at least one surface of the mask body is at least partially coated with a water impervious material.

In various exemplary embodiments, each ear loop comprises Spandex polyester, an elastic material, or a semi-elastic material.

In various exemplary embodiments, at least a portion of the mask body is bordered by stitching or heat welding.

In various exemplary embodiments, at least a portion of each of the scent diffusing areas is bordered by stitching or heat welding. Alternatively, each of the scent diffusing areas is completely bordered by stitching or heat welding.

In various exemplary embodiments, each of the scent diffusing areas is capable of being at least partially infused with a liquid containing an aroma compound. Each of the scent diffusing areas may optionally be unscented or may be at least partially infused with an aroma compound.

In various exemplary embodiments, each of the scent diffusing areas is defined by an aperture formed through the mask body and wherein a portion of material is attached or coupled within each of the apertures to form the scent diffusing areas.

In various exemplary, non-limiting embodiments, the sleep mask of the present disclosure comprises a mask body having a central portion formed between two extension portions, wherein the mask body comprises two or more layers of material at least partially attached or coupled together; an ear loop extending from each of the extension portions, wherein each ear loop is attached or coupled to the extension portion proximate terminal ends of the ear loop; and a scent diffusing area formed within each of the extension portions, wherein each of the scent diffusing areas is capable of being at least partially infused with an aroma compound.

In various exemplary embodiments, each of the scent diffusing areas is defined by an aperture formed through at least one of the layers of the mask body and wherein a portion of material is attached or coupled within each of the apertures to form the scent diffusing areas.

In various exemplary, non-limiting embodiments, the sleep mask of the present disclosure comprises a mask body having a central portion formed between two extension portions, wherein the mask body comprises two or more layers of material at least partially attached or coupled together; an ear loop extending from each of the extension portions, wherein each ear loop comprises an elastic or semi-elastic material, and wherein each ear loop is attached or coupled to the extension portion proximate terminal ends of the ear loop; and a scent diffusing area formed within each of the extension portions, wherein each of the scent diffusing areas is capable of being at least partially infused with an aroma compound, and wherein a pillowing material is positioned between the layers of material within at least a portion of each of the scent diffusing areas.

Accordingly, the present disclosure separately and optionally provides a room darkening sleep mask.

The present disclosure separately and optionally provides a sleep mask that is more sanitary than present sleep masks.

The present disclosure separately and optionally provides a sleep mask that is disposable.

The present disclosure separately and optionally provides a sleep mask that can be packaged and dispensed from a box.

The present disclosure separately and optionally provides a sleep mask having soft ear loops that reduce or eliminate pressure to the wearer's ears and/or head.

The present disclosure separately and optionally provides a sleep mask that can be worn without leaving intentions in the wearer's hair.

The present disclosure separately and optionally provides a sleep mask that comprises a lightweight, breathable fiber that eliminates pressure to the wearer's eyes, for increased comfort.

The present disclosure separately and optionally provides a sleep mask that can be unscented.

The present disclosure separately and optionally provides a sleep mask that is capable of being at least partially infused with an aroma compound.

These and other aspects, features, and advantages of the present disclosure are described in or are apparent from the following detailed description of the exemplary, non-limiting embodiments of the present disclosure and the accompanying figures. Other aspects and features of embodiments of the present disclosure will become apparent to those of ordinary skill in the art upon reviewing the following description of specific, exemplary embodiments of the present disclosure in concert with the figures. While features of the present disclosure may be discussed relative to certain embodiments and figures, all embodiments of the present disclosure can include one or more of the features discussed herein. Further, while one or more embodiments may be discussed as having certain advantageous features, one or more of such features may also be used with the various embodiments of the systems, methods, and/or apparatuses discussed herein. In similar fashion, while exemplary embodiments may be discussed below as device, system, or method embodiments, it is to be understood that such exemplary embodiments can be implemented in various devices, systems, and methods of the present disclosure.

Any benefits, advantages, or solutions to problems that are described herein with regard to specific embodiments are not intended to be construed as a critical, required, or essential feature(s) or element(s) of the present disclosure or the claims.

BRIEF DESCRIPTION OF THE SEVERAL VIEWS OF THE DRAWINGS

As required, detailed exemplary embodiments of the present disclosure are disclosed herein; however, it is to be understood that the disclosed embodiments are merely exemplary of the present disclosure that may be embodied in various and alternative forms, within the scope of the present disclosure. The figures are not necessarily to scale; some features may be exaggerated or minimized to illustrate details of particular components. Therefore, specific structural and functional details disclosed herein are not to be interpreted as limiting, but merely as a basis for the claims and as a representative basis for teaching one skilled in the art to employ the present disclosure.

The exemplary embodiments of the present disclosure will be described in detail, with reference to the following figures, wherein like reference numerals refer to like parts throughout the several views, and wherein.

DETAILED DESCRIPTION OF EXEMPLARY EMBODIMENTS OF THE PRESENT DISCLOSURE

For simplicity and clarification, the design factors of the sleep mask according to the present disclosure are explained with reference to various exemplary embodiments of a sleep mask. The basic explanation of the design factors of the sleep mask is applicable for the understanding, design, and operation of the sleep mask of the present disclosure. It should be appreciated that the sleep mask can be adapted to many applications where a sleep or other mask can be used.

As used herein, the word "may" is meant to convey a permissive sense (i.e., meaning "having the potential to"), rather than a mandatory sense (i.e., meaning "must"). Unless stated otherwise, terms such as "first" and "second" are used to arbitrarily distinguish between the exemplary embodiments and/or elements such terms describe. Thus, these terms are not necessarily intended to indicate temporal or other prioritization of such exemplary embodiments and/or elements.

The term "coupled", as used herein, is defined as connected, although not necessarily directly, and not necessarily mechanically. The terms "a" and "an" are defined as one or more unless stated otherwise.

Throughout this application, the terms "comprise" (and any form of comprise, such as "comprises" and "comprising"), "have" (and any form of have, such as "has" and "having"), "include", (and any form of include, such as "includes" and "including") and "contain" (and any form of contain, such as "contains" and "containing") are used as open-ended linking verbs. It will be understood that these terms are meant to imply the inclusion of a stated element, integer, step, or group of elements, integers, or steps, but not the exclusion of any other element, integer, step, or group of elements, integers, or steps. As a result, a system, method, or apparatus that "comprises", "has", "includes", or "contains" one or more elements possesses those one or more elements but is not limited to possessing only those one or more elements. Similarly, a method or process that "comprises", "has", "includes" or "contains" one or more operations possesses those one or more operations but is not limited to possessing only those one or more operations.

It should also be appreciated that the terms "sleep mask" and "mask" are used for basic explanation and understanding of the operation of the present disclosure. Therefore, the terms "sleep mask" and "mask" are not to be construed as limiting the present disclosure. Thus, the terms "sleep mask" and "mask" are to be understood to broadly include any elongate portion of material capable of being worn to cover at least a portion of a wearer's face.

Figure 1:
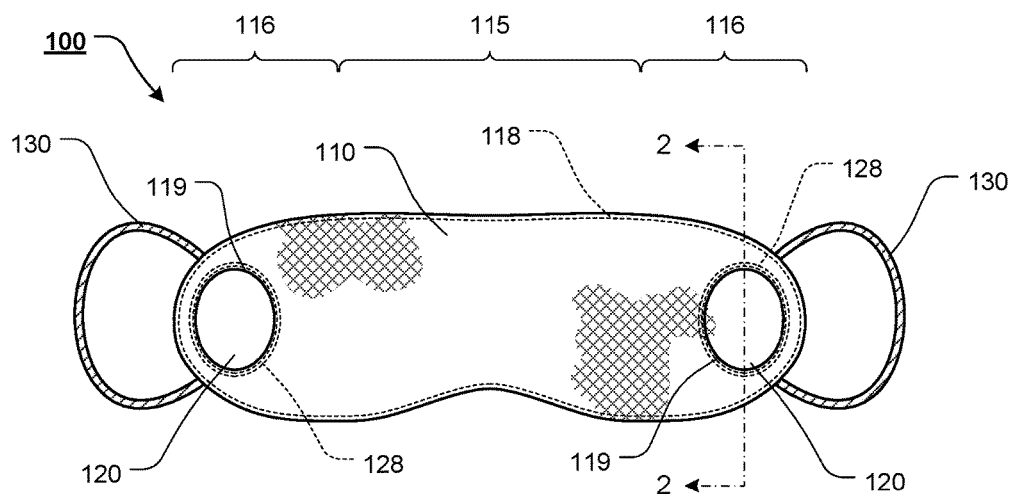
FIG. 1 illustrates a front view of an exemplary embodiment of the sleep mask, according to the present disclosure.
Figure 2:
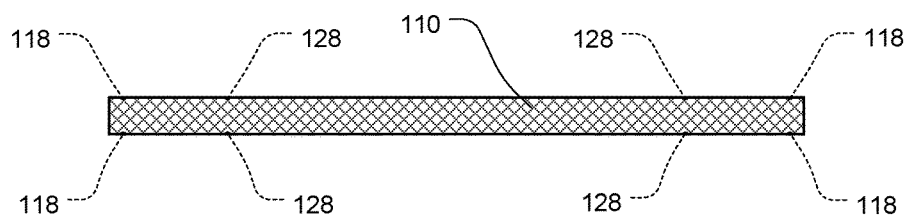
FIG. 2 illustrates a side cross-sectional view taken along line 2-2 of the sleep mask of FIG. 1.
Figure 3:
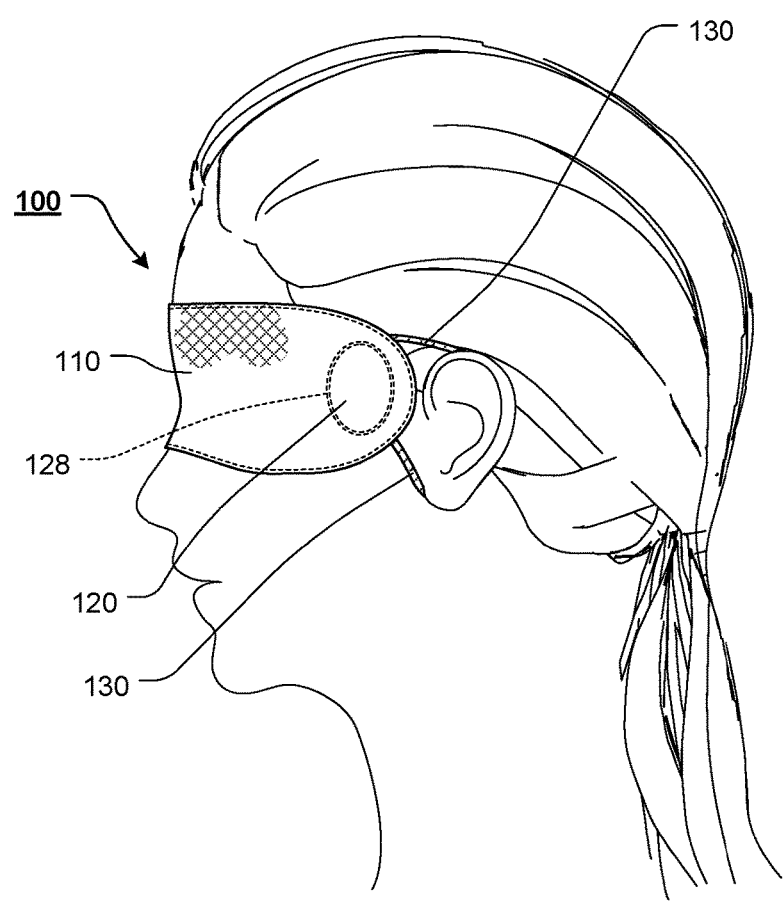
FIG. 3 illustrates a side view of an exemplary embodiment of the sleep mask, according to the present disclosure, wherein the sleep mask is illustrated as being worn by a wearer.
Figure 4:
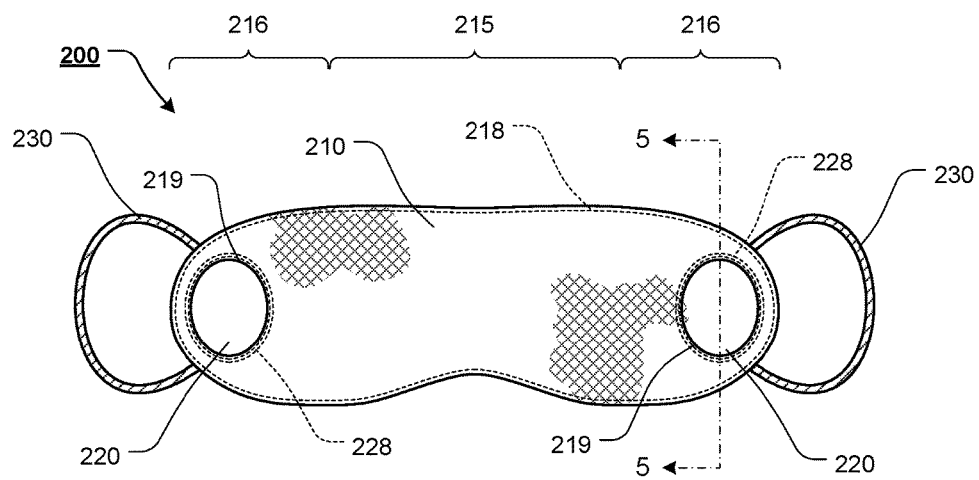
FIG. 4 illustrates a front view of an exemplary embodiment of the sleep mask, according to the present disclosure.
Figure 5:
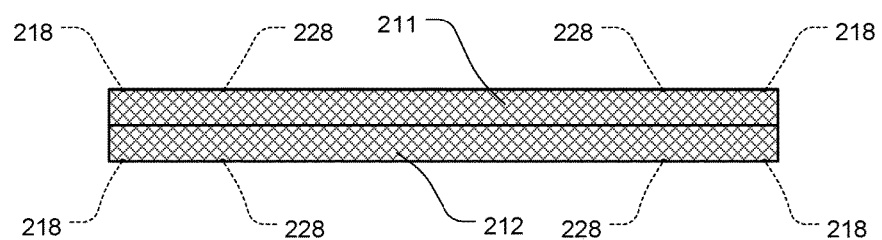
FIG. 5 illustrates a side cross-sectional view taken along line 5-5 of the sleep mask of FIG. 4.
Figure 6:
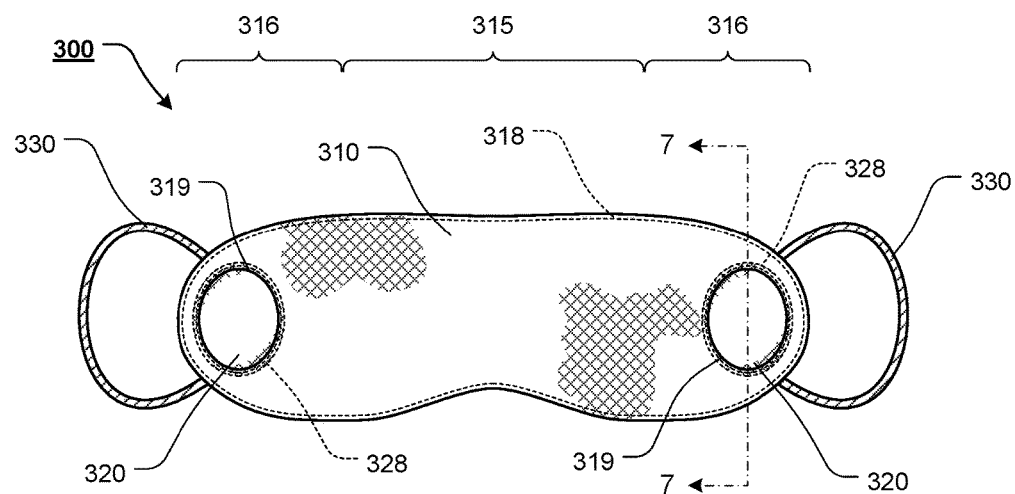
FIG. 6 illustrates a front view of an exemplary embodiment of the sleep mask, according to the present disclosure.
Figure 7:
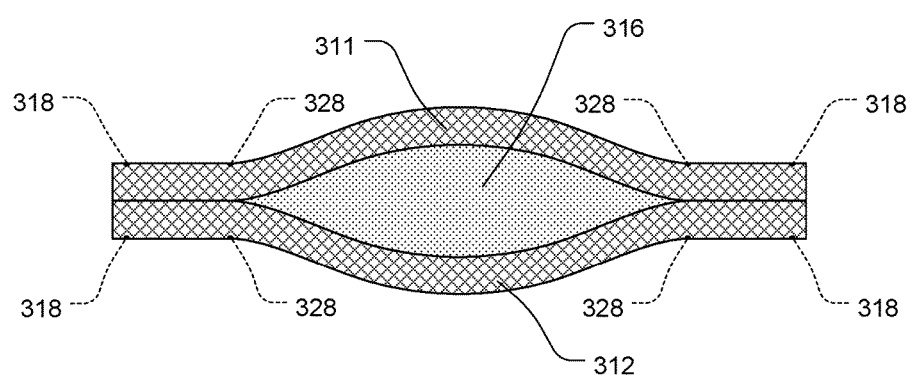
FIG. 7 illustrates a side cross-sectional view taken along line 7-7 of the sleep mask of FIG. 6.

Turning now to the appended drawing figures, FIGS. 1-3 illustrate certain elements and/or aspects of an exemplary embodiment of the sleep mask 100, FIGS. 4-5 illustrate certain elements and/or aspects of an exemplary embodiment of the sleep mask 200, while FIGS. 6-7 illustrate certain elements and/or aspects of an exemplary embodiment of the sleep mask 300 of the present disclosure. It should be understood that while FIGS. 1, 4, and 6 illustrate front views of the sleep mask 100, sleep mask 200, and sleep mask 300, the rear views of the sleep mask 100, sleep mask 200, and/or the sleep mask 300 may optionally be identical or substantially similar to the front views of the sleep mask.

In illustrative, non-limiting embodiment(s) of the present disclosure, as illustrated in FIGS. 1-3, the sleep mask 100 comprises at least some of a mask body 110, ear loops 130, and scent diffusing areas 120. The mask body 100 generally comprises an elongate portion of material and includes a central portion 115 formed between two extension portions 116. The central portion 115 is generally arranged such that when the sleep mask 100 is worn by a wearer, as illustrated in FIG. 3, the central portion 115 generally covers the wearer's eyes. The extension portions 116 extend from the central portion 115, such that when the sleep mask 100 is worn, the extension portions 116 each extend to cover at least a portion of the wearer's temple area, generally located in the areas between the user's eyes and ears.

In certain exemplary embodiments, the mask body 110 comprises a single layer of a continuous portion of material. In various exemplary, nonlimiting embodiments, the single layer of material may optionally be formed of a Polyspunbond material, a Spunbond Polypropylene material, a Spunbond Polyester material, a single layer nonwoven material, or a multilayer nonwoven material formed as a single layer. It should be appreciated that the mask body 110 may be formed of a material that is at least partially or completely water impervious or water absorbent.

If desired, at least one surface of the mask body 110 may optionally be at least partially coated with a water impervious material. Alternatively, various portions of various surfaces of the mask body 110 may optionally be at least partially coated with a water pervious material.

If desired, portions or an entire outer perimeter of the mask body 110 may be bordered by stitching or heat welding elements 118.

An ear loop 130 extends from each of the extension portions 116. Each ear loop 130 comprises a length of elastic or semi-elastic material. In various exemplary embodiments, each ear loop 130 comprises spandex polyester. Each ear loop 130 is attached or coupled to a respective extension portion 116 at terminal ends or end portions of the ear loop 130. In certain exemplary embodiments, each ear loop 130 is attached or coupled to a respective extension portion 116 via an adhesive attachment, stitching, or heat welding of portions of each of the ear loops 130 to the mask body 110.

Scent diffusing areas 120 are formed within each extension portion 116. The overall size and shape of each scent diffusing area 120 is a design choice and the generally oval-shaped scent diffusing areas 120, depicted in FIGS. 1 and 3 are to be understood to be illustrative and not limiting. The scent diffusing areas 120 are generally formed within an area of each extension portion 116 that is proximate a wearer's temple, when the sleep mask 100 is worn.

Each of the scent diffusing areas 120 is capable of being at least partially infused with a liquid containing an aroma compound. Each of the scent diffusing areas 120 may optionally be bordered by stitching or heat welding elements 128. The stitching or heat welding elements 128 may completely surround and encompass each scent diffusing area 120 or may only partially surround or border each scent diffusing area 120. If included, the stitching or heat welding elements 128 may act to help maintain an aroma compound within the designated scent diffusing areas 120.

In certain exemplary embodiments, the sleep mask 100 can be originally supplied with each scent diffusing area 120 being at least partially infused with an aroma compound. Alternatively, the sleep mask 100 may be originally supplied without any aroma compound, so that a wearer can choose to infuse a desired aroma compound in the scent diffusing areas 120.

In certain exemplary embodiments, the scent diffusing areas 120 merely comprise designated areas within the material used to form the mask body 110. Alternatively, the mask body 110 may be formed of a material having windows or apertures 119 (not illustrated in FIG. 2) formed in the areas of the scent diffusing areas 120. In these embodiments, and alternate or a different material from the material used to form the mask body 110 is attached or coupled within the windows or apertures 119 in the areas of the scent diffusing areas 120. If a different material is used to form the scent diffusing areas 120, the material of the scent diffusing areas 120 may be attached or coupled to the mask body 110, within the windows or apertures 119, via, for example, adhesive attachment, stitching, heat welding, ultrasonic welding, or the like. In certain embodiments, the materials used to form the scent diffusing areas 120 may be at least partially attached or coupled to the mask body 110, via the stitching or heat welding elements 128.

The aroma compound utilized within the designated scent diffusing areas 120 may optionally be an essential oil, formed of a concentrated hydroponic liquid containing one or more volatile aroma compounds. Essential oils, volatile oils, ethereal oils, aetherolea, and the like, are generally known in aromatherapy. In certain exemplary embodiments, the aroma compound may comprise a lavender scented oil or compound.

When the sleep mask 100 is worn, the central portion 115 is positioned generally in front of the wearer's eyes and each ear loop 130 is positioned around and behind a wearer's ear. This generally positions the extension portions 116 and the scent diffusing areas 120 in an area proximate each of the wearer's temples.

FIGS. 4-5 illustrate an exemplary embodiment of a sleep mask 200, according to the present disclosure. As shown in FIGS. 4-5, the sleep mask 200 comprises at least some of a mask body 210 having a central portion 215 and two extension portions 216, optional stitching or heat welding elements 218, optional apertures 219 (not illustrated in FIG. 5), ear loops 230, scent diffusing areas 220, and optional stitching or heat welding elements 228.

It should be understood that each of these elements corresponds to and operates similarly to the mask body 110, the central portion 115, the two extension portions 116, the optional stitching or heat welding elements 118, the optional apertures 119, the ear loops 130, the scent diffusing areas 120, and the optional stitching or heat welding elements 128, as described above with reference to the sleep mask 100 of FIGS. 1-3.

However, as shown in FIGS. 4-5, the sleep mask 200 comprises a mask body 210 having a first layer of material 211 and a second layer of material 212. The first layer 211 and the second layer 212 are at least partially attached or coupled to one another to form the mask body 210. In certain embodiments, the first layer 211 and the second layer 212 are at least partially attached or coupled to one another, via the stitching or heat welding elements 218.

If included, the optional windows or apertures 219 formed in the areas of the scent diffusing areas 220 may only be formed into the first layer 211 or the second layer 212. Alternatively, the optional windows or apertures 219 may be formed through both the first layer 211 and the second layer 212. One or more materials may then be attached or coupled to the first layer 211 and/or the second layer 212, within the windows or apertures 219 to form the scent diffusing areas 220. In certain embodiments, the materials used to form the scent diffusing areas 220 may be at least partially attached or coupled to the respective first layer 211 and/or second layer 212, via the stitching or heat welding elements 228.

FIGS. 6-7 illustrate an exemplary embodiment of a sleep mask 300, according to the present disclosure. As shown in FIGS. 6-7, the sleep mask 300 comprises at least some of a mask body 310 having a central portion 315, two extension portions 316, a first layer 311, and a second layer 312, optional stitching or heat welding elements 318, optional apertures 319 (not illustrated in FIG. 7), ear loops 330, scent diffusing areas 320, and optional stitching or heat welding elements 328.

It should be understood that each of these elements corresponds to and operates similarly to the mask body 210, the first layer 211, the second layer 212, the central portion 215, the two extension portions 216, the optional stitching or heat welding elements 218, the optional apertures 219, the ear loops 230, the scent diffusing areas 220, and the optional stitching or heat welding elements 228, as described above with reference to the sleep mask 100 of FIGS. 1-3.

However, as shown in FIGS. 6-7, a pillowing material 316 is positioned between the first layer 311 and the second layer 312 within each of the scent diffusing areas 320. The pillowing material 316 provides a protruding or bulged area forming at least a portion of the scented diffusing areas 320. The pillowing material 316 may also be at least partially infused with or infusible with an aroma compound.

While the present disclosure has been described in conjunction with the exemplary embodiments outlined above, the foregoing description of exemplary embodiments of the present disclosure, as set forth above, are intended to be illustrative, not limiting and the fundamental disclosed systems, methods, and/or apparatuses should not be considered to be necessarily so constrained. It is evident that the present disclosure is not limited to the particular variation set forth and many alternatives, adaptations modifications, and/or variations will be apparent to those skilled in the art.

Furthermore, where a range of values is provided, it is understood that every intervening value, between the upper and lower limit of that range and any other stated or intervening value in that stated range is encompassed within the present disclosure. The upper and lower limits of these smaller ranges may independently be included in the smaller ranges and is also encompassed within the present disclosure, subject to any specifically excluded limit in the stated range. Where the stated range includes one or both of the limits, ranges excluding either or both of those included limits are also included in the present disclosure.

It is to be understood that the phraseology of terminology employed herein is for the purpose of description and not of limitation. Unless defined otherwise, all technical and scientific terms used herein have the same meaning as commonly understood by one of ordinary skill in the art to which the present disclosure belongs.

In addition, it is contemplated that any optional feature of the inventive variations described herein may be set forth and claimed independently, or in combination with any one or more of the features described herein.

Accordingly, the foregoing description of exemplary embodiments will reveal the general nature of the present disclosure, such that others may, by applying current knowledge, change, vary, modify, and/or adapt these exemplary, non-limiting embodiments for various applications without departing from the spirit and scope of the present disclosure and elements or methods similar or equivalent to those described herein can be used in practicing the present disclosure. Any and all such changes, variations, modifications, and/or adaptations should and are intended to be comprehended within the meaning and range of equivalents of the disclosed exemplary embodiments and may be substituted without departing from the true spirit and scope of the present disclosure.

Also, it is noted that as used herein and in the appended claims, the singular forms "a", "and", "said", and "the" include plural referents unless the context clearly dictates otherwise. Conversely, it is contemplated that the claims may be so-drafted to require singular elements or exclude any optional element indicated to be so here in the text or drawings. This statement is intended to serve as antecedent basis for use of such exclusive terminology as "solely", "only", and the like in connection with the recitation of claim elements or the use of a "negative" claim limitation(s).

What is claimed is:

1. A sleep mask, comprising:
   a mask body having a central portion formed between two extension portions;
   an ear loop extending from each of said extension portions, wherein each ear loop is attached or coupled to said extension portion proximate terminal ends of said ear loop; and
   a scent diffusing area formed within each of said extension portions, wherein said scent diffusing area is bordered by stitching or heat welding elements, and wherein each of said scent diffusing areas is capable of being at least partially infused with an aroma compound.

2. The sleep mask of claim 1, wherein said mask body is a continuous mask body.

3. The sleep mask of claim 1, wherein said mask body comprises Polyspunbond, Spunbond Polypropylene, Spunbond Polyester, a single layer nonwoven material, or a multilayer nonwoven material.

4. The sleep mask of claim 1, wherein said mask body comprises a single layer of material.

5. The sleep mask of claim 1, wherein at least one surface of said mask body is at least partially coated with a water impervious material.

6. The sleep mask of claim 1, wherein said mask body comprises two or more layers of material at least partially attached or coupled together.

7. The sleep mask of claim 1, wherein each ear loop comprises Spandex polyester, an elastic material, or a semi-elastic material.

8. The sleep mask of claim 1, wherein at least a portion of each of said scent diffusing areas is bordered by stitching or heat welding.

9. The sleep mask of claim 1, wherein each of said scent diffusing areas is bordered by stitching or heat welding.

10. The sleep mask of claim 1, wherein each of said scent diffusing areas is capable of being at least partially infused with a liquid containing an aroma compound.

11. The sleep mask of claim 1, wherein each of said scent diffusing areas is at least partially infused with an aroma compound.

12. The sleep mask of claim 1, wherein each of said scent diffusing areas is defined by an aperture formed through said mask body and wherein a portion of material is attached or coupled within each of said apertures to form said scent diffusing areas.

13. A sleep mask, comprising:
   a mask body having a central portion formed between two extension portions, wherein said mask body comprises two or more layers of material at least partially attached or coupled together;
   an ear loop extending from each of said extension portions, wherein each ear loop is attached or coupled to said extension portion proximate terminal ends of said ear loop; and
   a scent diffusing area formed within each of said extension portions, wherein said scent diffusing area is bordered by stitching or heat welding elements, and wherein each of said scent diffusing areas is capable of being at least partially infused with an aroma compound.

14. The sleep mask of claim 13, wherein each of said layers of said mask body comprises Polyspunbond, Spunbond Polypropylene, Spunbond Polyester, a single layer nonwoven material, or a multilayer nonwoven material.

15. The sleep mask of claim 13, wherein each of the scent diffusing areas is defined by an aperture formed through at least one of said layers of said mask body and wherein a portion of material is attached or coupled within each of said apertures to form said scent diffusing areas.

16. The sleep mask of claim 13, wherein a pillowing material is positioned between said layers of material within at least a portion of each of said scent diffusing areas.

17. The sleep mask of claim 13, wherein each of said scent diffusing areas is bordered by stitching or heat welding.

18. The sleep mask of claim 13, wherein each of said scent diffusing areas is capable of being at least partially infused with a liquid containing an aroma compound.

19. The sleep mask of claim 13, wherein each of said scent diffusing areas is at least partially infused with an aroma compound.

20. A sleep mask, comprising:
   a mask body having a central portion formed between two extension portions, wherein said mask body comprises two or more layers of material at least partially attached or coupled together;
   an ear loop extending from each of said extension portions, wherein each ear loop comprises an elastic or semi-elastic material, and wherein each ear loop is attached or coupled to said extension portion proximate terminal ends of said ear loop;
   a scent diffusing area formed within each of said extension portions, wherein said scent diffusing area is bordered by stitching or heat welding elements, wherein each of said scent diffusing areas is capable of being at least partially infused with an aroma compound, and wherein a pillowing material is positioned between said layers of material within at least a portion of each of said scent diffusing areas.

* * * * *